United States Patent [19]

Carim et al.

[11] Patent Number: 5,795,293

[45] Date of Patent: Aug. 18, 1998

[54] REDUCING ARTIFACT IN BIOELECTRIC SIGNAL MONITORING

[75] Inventors: Hatim M. Carim, West St. Paul, Minn.; Scott A. Burton, Essex Junction, Vt.

[73] Assignee: Minnesota Mining and Manufacturing Company, St. Paul, Minn.

[21] Appl. No.: 586,011

[22] Filed: Dec. 29, 1995

[51] Int. Cl.$^6$ .................................................. A61B 5/04
[52] U.S. Cl. ........................................ 600/372; 128/898
[58] Field of Search ......................... 128/639–641, 128/643, 644, 734, 696, 700, 898; 607/2, 75, 50, 149, 100, 98, 99, 72, 66

[56] References Cited

U.S. PATENT DOCUMENTS

| | | | |
|---|---|---|---|
| 4,149,527 | 4/1979 | Naylor et al. | |
| 4,372,319 | 2/1983 | Ichinomiya et al. | 607/72 |
| 4,406,827 | 9/1983 | Carim | 252/518 |
| 4,574,813 | 3/1986 | Regan | 128/697 |
| 4,664,116 | 5/1987 | Shaya et al. | |
| 4,838,278 | 6/1989 | Wang et al. | 128/697 |
| 4,846,185 | 7/1989 | Carim | 128/641 |
| 4,934,376 | 6/1990 | Armington | 128/696 |
| 4,950,378 | 8/1990 | Nagata | 204/402 |
| 4,977,895 | 12/1990 | Tannenbaum | 607/66 |
| 5,003,987 | 4/1991 | Grinwald | 128/734 |
| 5,205,284 | 4/1993 | Freeman | |
| 5,285,792 | 2/1994 | Sjoquist et al. | 128/697 |
| 5,311,658 | 5/1994 | Shimizu | 29/746 |
| 5,333,617 | 8/1994 | Hafner | 128/697 |
| 5,381,351 | 1/1995 | Kwong et al. | 364/571.04 |

FOREIGN PATENT DOCUMENTS

| | | |
|---|---|---|
| 551 746 A2 | 7/1993 | European Pat. Off. |
| 571 120 A1 | 11/1993 | European Pat. Off. |
| 1 812 314 | 6/1970 | Germany |
| 1547808 A1 | 7/1990 | U.S.S.R. |
| WO 94/26950 | 11/1994 | WIPO |

OTHER PUBLICATIONS

Edelberg, "Electrical Properties of Skin" *A Treatise of Skin*, vol. 1 *Biophysical Properties of Skin* (Wiley Interscience 1971) pp. 513–550.

Harris, "Iontophoresis" *Therapeutic Electricity and Ultraviolet Radiation* (Krieger 1967) pp. 156–163.

D.P. Burbank et al., "Reducing skin potential motion artefact by skin abrasion", *Med. & Biol. Eng. & Comput.*, 16, 31–38 (1978).

H.M. Carim, "Bioelectrodes" in *Encyclopedia of Medical Devices and Instrumentation*, vol. 1; J.G. Webster, Ed.; Wiley & Sons: New York; pp. 195–226.

"Pharmacologic Effects on the Sweat Glands" in *Advances in Modern Toxicology*, vol. 4, *Dermatotoxicology and Pharmacology*; F.N. Marzulli et al., Eds.; Hemisphere Publishing: Washington; pp. 3–4.

H.I. Maibach et al., "Noninvasive Techniques for Determining Skin Function", in *Cutaneous Toxicity*; V.A. Drill et al., Eds.; Raven Press: New York; pp. 63–97 (1984).

J.G. Webster, "How to prevent 60–Hz interference", *Medical Instrumentation*, 13, 302–303 (Sep.–Oct. 1979).

J.G. Webster, "Interference and Motion Artifact in Biopotentials", *IEEE Region 6 1987 Conference*, pp. 53–64 (1987).

B.B. Winter et al., "Driven–Right–Leg Circuit Design", *IEEE Transactions on Biomedical Engineering*, BME–30, 62–66 (Jan. 1983).

B.B. Winter et al., "Reduction of Interference Due to Common Mode Voltage in Biopotential Amplifiers", *IEEE Transactions on Biomedical Engineering*, BME–30, 58–61 (Jan. 1983).

*Primary Examiner*—Jennifer Bahr
*Assistant Examiner*—Bryan K. Yarnell
*Attorney, Agent, or Firm*—Gary L. Griswold; Walter N. Kirn; John H. Hornickel

[57] ABSTRACT

Systems and methods of conditioning skin to reduce artifact in bioelectric signal monitoring by passing electrical energy into the skin through the medical electrodes. An electrode having electrolyte including an agent to reduce skin discomfort.

10 Claims, 7 Drawing Sheets

REDUCING ARTIFACT IN BIOELECTRIC SIGNAL MONITORING

FIELD OF THE INVENTION

The present invention relates to the field of monitoring bioelectrical signals using medical electrodes. More particularly, the present invention relates to systems and methods of conditioning skin to reduce artifact in bioelectric signal monitoring.

BACKGROUND OF THE INVENTION

Bioelectric signals, including bioelectric potentials and/or bioelectric currents, are monitored and recorded using skin-mounted electrodes to assist in the diagnosis and treatment of many different medical illnesses and conditions.

One example of a bioelectric signal monitored using medical electrodes is the electrical activity of the heart recorded in the form of an electrocardiogram (ECG). The bioelectric signal activity is typically displayed as voltage ($\Delta V_{Heart}$). The signal ultimately displayed is the composite of several different potentials in addition to those generated by the heart muscle ($\Delta V_{Heart} + \Delta V_{noise}$).

The fidelity of the signal generated using medical electrodes to accurately conform to the monitored bioelectric signal is typically referred to as trace quality. Trace quality can be represented by the following equation:

$$\text{Trace Quality} = \Delta V_{Heart} / (\Delta V_{Heart} + \Delta V_{noise}) \quad \text{(Equation 1)}$$

The change in measured potential due to noise ($\Delta V_{noise}$) is a combination of a variety of different "artifacts" caused by deformation of the skin, static electricity, induced potentials due to alternating current power sources, radio frequency sources, muscle activity, magnetic fields and triboelectric potentials. These factors all reduce the trace quality of signals produced using medical electrodes placed on a patient's skin to monitor bioelectric signals. John G. Webster, "Interference and Motion Artifact in Biopotentials," *IEEE Region 6*, 1987 Conference, pp. 53–64, discusses these artifacts and some of the approaches used to reduce their effect on trace quality.

Some of the artifacts, such as those caused by static electricity, alternating current electrical power sources, and radio frequency interference can be reduced using a variety of known methods. One method useful for reducing several of the artifacts is hydration of the skin beneath the electrodes. That hydration occurs spontaneously due to the lower evaporative losses of the skin beneath the monitoring electrodes as well as moisture absorbed from the gels or other electrolyte materials used with many electrodes.

Electronic shielding is also useful to reduce triboelectric potentials in addition to those caused by static electricity, alternating current electrical power sources, and radio frequency interference.

Special circuitry and electrode configurations, typically referred to as a driven-right-leg circuit effectively reduces artifact caused by alternating current power sources. The circuitry essentially involves passing a very small amount of electrical energy into the patient that is out of phase with the induced potentials due to alternating current power sources. This circuitry is described by Winter et al. in "Driven-Right-Leg Circuit Design," *IEEE Transactions on Biomedical Engineering*, Vol. BME-30, No. 1, January 1983.

Although these approaches at reducing artifacts help to improve trace quality by reducing $\Delta V_{Noise}$, they do not address skin impedance which significantly affects the magnitude of skin deformation artifact. Several approaches have been developed to reduce skin impedance and, thereby, also reduce skin deformation artifact. One approach involves abrading the skin in the area in which an electrode is applied. By abrading skin, the stratum corneum layer is reduced or, in some instances, removed. By reducing the thickness of the stratum corneum, the deformation artifact can be reduced.

Although abrasion is helpful, it can result in large welts and/or scabbing, particularly when performed by an inexperienced operator. At the other end of the spectrum, an inexperienced operator may fail to sufficiently abrade the skin in the desired area, thereby minimally reducing the amount of deformation artifact experienced during monitoring.

Additional drawbacks of the abrasion approach include the additional steps required by the operator to abrade the skin, itching and/or stinging of the abraded skin due to the salts contained in the electrolytes used with many electrodes, as well as the costs associated with providing the materials needed to abrade the skin.

Furthermore, if the operator fails to sufficiently reduce skin impedance through abrasion, the electrode must then be removed from the site and discarded, further abrasion of the skin performed, and then a new electrode must be applied. These additional steps all increase the cost of the procedure, the discomfort of the patient and amount of materials to be disposed.

Another approach at reducing deformation artifact includes increasing the surface area contact between the monitoring electrode and the patient. Cost is a significant disadvantage of this approach because increasing the size of the electrodes increases their cost. In addition, depending on the bioelectric signal to be monitored, it may be difficult or impossible to increase the size of the electrodes sufficiently to significantly reduce the deformation artifact.

Yet another approach at reducing deformation artifact involves piercing the patient's skin in a plurality of locations beneath a monitoring electrode. One mechanism for accomplishing that piercing is disclosed in EPO Publication No. 0 571 120 A1. Although piercing the patient's skin can help reduce deformation artifact, it can also cause irritation and redness or swelling after the procedure has been completed. In addition, in emergency situations, the operator may forget to pierce the skin of the patient or may fail to adequately pierce the stratum corneum to realize the benefits of this procedure, thereby relying on readings that may not be as accurate as expected.

Another approach at reducing deformation artifact includes providing additional chloride ions ($Cl^-$) between the skin and electrode to increase conductivity through the stratum corneum. Drawbacks of this approach include additional irritation caused by the chloride ions, as well as the additional steps needed to prepare the site and the cost of materials and time. When used in combination with abrasion or piercing, the additional chloride ions can exacerbate stinging and irritation.

SUMMARY OF THE INVENTION

The present invention involves systems and methods of conditioning skin to reduce artifact in bioelectric signal monitoring by passing electrical energy into the skin through the medical electrodes.

The methods according to the present invention involve directing electrical energy through a medical electrode placed on the skin of a patient to monitor bioelectric signals. The electrical energy is delivered as a conditioning current that can be provided in any suitable waveform in which amplitude and/or polarity are constant or vary over time. In one preferred method, the conditioning currents are anodic direct currents.

Systems according to the present invention can include circuits and controls separate from bioelectric signal monitoring equipment or the two can be integrated into a single unit. In either case, the systems preferably isolate the monitoring circuits during application of the conditioning currents to protect them from damage. In addition, it is preferred that the conditioning current source is programmable to allow the operator to selectively and automatically apply the conditioning currents at the desired intervals and with the appropriate waveforms.

The present invention also includes electrodes having electrolyte including an agent to reduce skin discomfort.

These and other features and advantages of systems and methods according to the present invention are discussed below.

DETAILED DESCRIPTION OF THE INVENTION

Skin impedance has a significant effect on the accuracy of measurements of bioelectric signals. The stratum corneum is a significant barrier to transmission of bioelectric signals across the skin to a medical electrode due to its relatively high resistance. The present invention provides systems and methods of conditioning skin to reduce artifact in bioelectric signal monitoring by passing electrical energy into the skin through the medical electrodes to reduce the skin impedance.

Although the skin with which the present invention is useful will typically be human skin, it will be understood that the systems and methods according to the present invention are equally applicable to the skin of any animal in which skin impedance is a concern in the monitoring of bioelectric signals.

Figure 1:
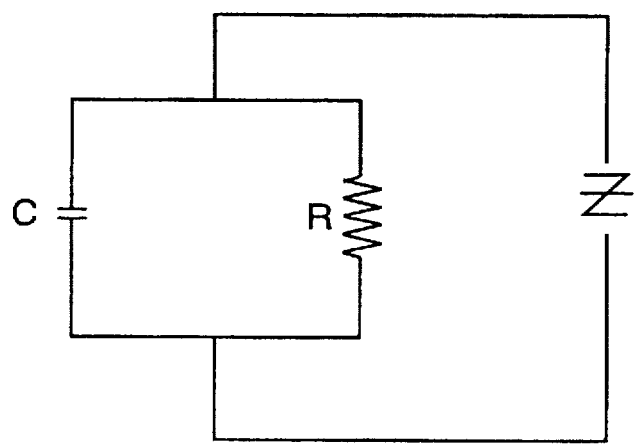
FIG. 1 is an equivalent circuit representing simplified electrical properties of the stratum corneum.

The electrical properties of the stratum corneum can be represented by the equivalent, simplified circuit presented in FIG. 1. As shown, skin impedance, Z, is a function of the capacitive and resistive nature of the stratum corneum. For direct currents and low frequency waveforms, the effect of the capacitive portion of the circuit is reduced and the impedance can be generally represented by resistance alone. Because resistance is relatively easily measured and serves as a relatively accurate measure of impedance for the electrical energy typically used in connection with the present invention, impedance will generally be discussed with reference to measured resistances below.

A significant factor that increases or affects deformation artifact when measuring bioelectric signals is skin impedance. When the skin (and the stratum corneum) beneath a monitoring electrode is deformed, e.g., by extension or compression, the skin impedance and the potential between the inside and outside layers of the skin varies.

A factor affecting skin impedance is the hydration level in the skin. For example, a typical electrocardiogram electrode-skin resistance at 10 Hz (due primarily to the stratum corneum) can be about 400K$\Omega$, but hydration can reduce the resistance to about 60K$\Omega$ over a period several minutes to several hours depending on a number of factors. The hydration occurs naturally under the electrodes due to reduced evaporative losses, as well as due to absorption of moisture/electrolyte from the gels or electrolytes used with the electrode.

Skin deformation artifact has two contributors that can be characterized by two different equations. The first equation is as follows:

$$\Delta V_{Phase\ 1} = i_{electrolyte} \cdot \Delta R_{stratum\ corneum} \quad \text{(Equation 2)}$$

where $i_{electrolyte}$ represents the differential diffusion of electrolyte into the skin. Typically, the magnitude of $i_{electrolyte}$ will not change during skin deformation. The magnitude of $\Delta R_{stratum\ corneum}$ will, however, change significantly during the skin deformation, thereby causing the change in voltage represented by Equation 2.

The magnitude of the component of skin deformation artifact characterized by Equation 2 will typically be reduced as an electrode has been in position over long periods of time because of the reduction in skin impedance (and, therefore, a reduction in the magnitude of $\Delta R_{stratum\ corneum}$). That reduction will however, be offset somewhat by an increase in $i_{electrolyte}$ due, in large part, to the reduced resistance.

Equation 3 characterizes the second contributor to skin deformation artifact and is presented as:

$$\Delta V_{Phase\ 2} = \Delta i_{streaming} \cdot R_{stratum\ corneum} \quad \text{(Equation 3)}$$

In this equation, $R_{stratum\ corneum}$ has essentially stabilized and the changing factor is $i_{streaming}$ which represents the changes in current passing through the electrode-skin interface as electric equilibrium is reestablished beneath the electrode after skin deformation.

Figure 2:
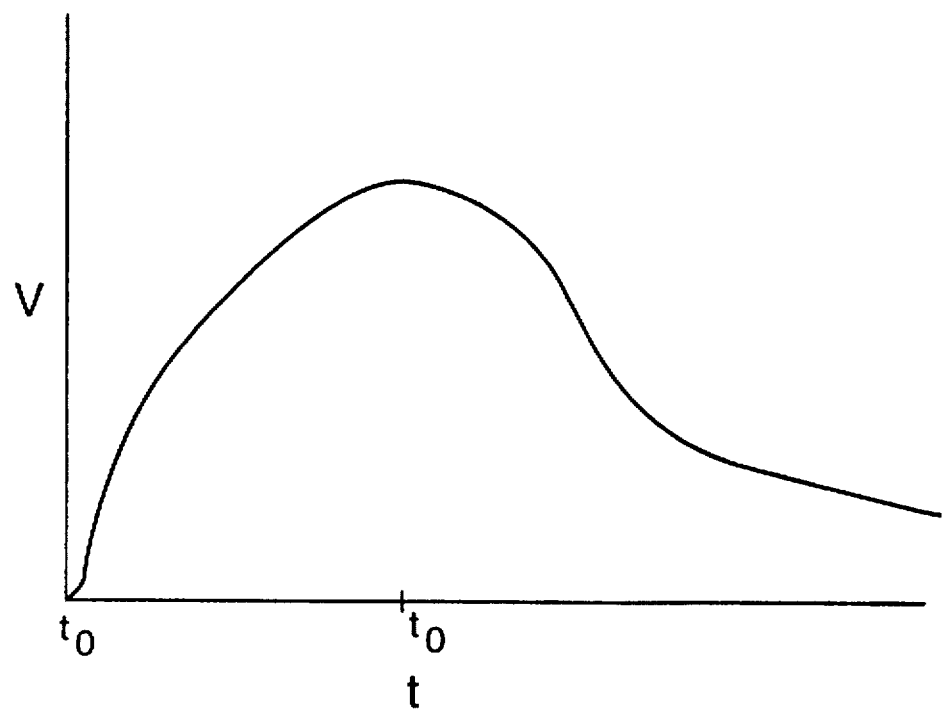
FIG. 2 is a graphical representation of the deformation artifact caused by skin deformation in real time.

FIG. 2 is a graphical representation of the combined skin deformation artifact represented by both $\Delta V_{Phase\ 1}$ and $\Delta V_{Phase\ 2}$. As shown, the deformation of skin between time $t_0$ and $t_1$ causes a rapid rise in deformation voltage followed by a decay of the deformation voltage artifact until equilibrium is reached. The component of skin deformation voltage artifact associated with $\Delta V_{Phase\ 1}$ decays faster than the skin deformation voltage artifact associated with $\Delta V_{Phase\ 2}$.

Both components of deformation artifact, i.e., $\Delta V_{Phase\ 1}$ and $\Delta V_{Phase\ 2}$, are reduced by the conditioning methods and systems according to the present invention. That conditioning can be measured by the reduction in skin impedance and the associated resistance that forms a part of the impedance.

It should be understood that the reduction of skin impedance provided by the systems and methods according to the present invention is only one measure of the conditioning of the skin beneath the electrode.

Figure 3:
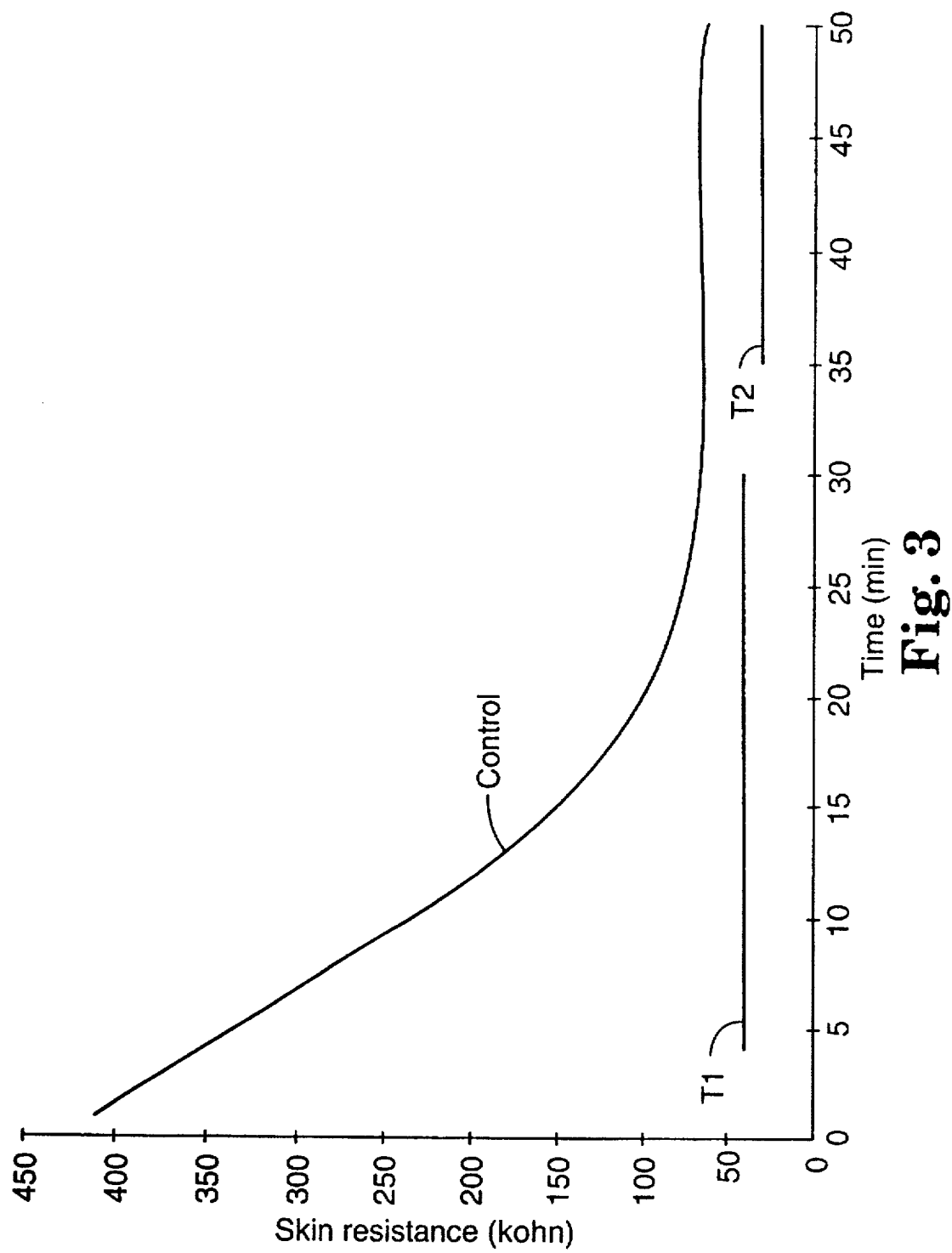
FIG. 3 is a graph of human skin resistance at 10 Hz as a function of time after application of a monitoring electrode with and without application of a conditioning current.

The quick and effective reduction of skin impedance is presented graphically in FIG. 3 which is a graph of resistance at the electrode-skin interface as a function of time after the application of a medical electrode. As shown, initial resistance beneath an electrode can be quite high, in the range of 400KΩ, although that resistance eventually decreases to about 60KΩ due primarily to skin hydration. These measurements were obtained using an alternating current with a frequency of about 10 Hz. Other methods of measuring resistance such as with a 100 nA direct current also show a proportional reduction in resistance. By applying a conditioning current through the electrodes, electrode-skin resistance can be quickly reduced to levels below those attained through hydration alone.

It should be noted that in some individuals, an increase in the resistance may be noted after application of a conditioning current. Those individuals, however, exhibited low initial resistances and any increases in resistance were not significant. Furthermore, these measurements may be subject to errors based on noise.

In addition to the reduction in skin resistance (which substantially corresponds to a reduction in skin impedance) FIG. 3 also depicts the effect of two applications of a conditioning current according to the present invention. As shown, skin resistance dropped to less than 50KΩ after the initial conditioning current (see line T1) and remained substantially constant. The second application of a conditioning current further reduced resistance below the levels achieved with the initial application of a conditioning current (see line T2).

The conditioning currents applied to achieve the results depicted in FIG. 3 consisted of application of an anodic direct current for one minute followed by application of a zero (0) milliamp rest interval of 30 seconds. It should be understood that the zero milliamp rest interval current is actively applied and will typically require application of a voltage to prevent induced currents through the electrode due to biopotentials and/or biocurrents.

Although the conditioning current used to generate the results depicted in FIG. 3 is an anodic direct current, it should be understood that it may also be desirable to apply the conditioning current in some other waveform that may involve varying amplitude and/or polarity over time. Examples of potential waveform variations can include, among others, sinusoidal waves, square waves, rectangular waves, saw-toothed waves, sinusoidal waves which do not reverse polarity, rectified sinusoidal waves, and arbitrary/random waveforms can also be used to condition the skin.

In addition to variations in the shapes of the waveforms, it may also be useful to ramp up the amplitude of the conditioning current over time. One example of a ramped conditioning current used involved ramping the current up to a maximum amplitude of about 0.33 mA/cm$^2$ over an initial period of 20 seconds based on voltage step increases of 8 V every five seconds until a maximum voltage level of 40 V was reached. Another ramping method used involved ramping voltage up to a maximum of 30 V in four steps of 7.5 V every five seconds. As one skilled in the art will appreciate, many other techniques of ramping up the current level may be used and, in addition, virtually any waveform could be ramped up to its maximum amplitude. Furthermore, at the end of the time during which the conditioning current is provided, it may be desirable to ramp the amplitude of the conditioning current down towards zero.

Although some waveforms used in connection with conditioning current may result in essentially no net charge passing through the electrode-skin interface, e.g., a balanced alternating current waveform with an average value of zero, it may be advantageous in some instances to provide for a net flow of charges in the positive or negative direction. Any direct current will, of course, provide that net flow and other waveforms that vary in amplitude and/or polarity, e.g., an alternating current with a direct current component, can also be provided to establish a net flow of charges in a desired direction if such a net flow is helpful.

In addition to waveforms and ramping, another variable in the application of a conditioning current is the amplitude of the waveform. Because the current is applied through an electrode having electrolyte with a defined skin contact surface area, current ranges will be expressed in terms of current/unit area to compensate for variations in electrolyte size. One preferred range of current amplitudes useful for conditioning the skin when using direct currents according to the present invention is from about 5 μA/cm$^2$ to about 5 mA/cm$^2$. More preferably, the current amplitudes are in the range from about 100 μA/cm$^2$ to about 1.5 mA/cm$^2$. It will be understood that if an alternating current or any other current that varies in amplitude and/or polarity is used in place of a direct current for conditioning, the root mean square (rms) values for that waveform equivalent to the ranges provided for direct currents above can be used to provided limits for the systems and methods according to the present invention.

It should also be understood that in situations where high frequencies, e.g., frequencies used in connection with electrosurgery equipment, the ranges discussed above may not apply due to the ability to pass currents with amplitudes that may be harmful if delivered at lower frequencies or as direct current.

Conditioning currents according to the present invention are provided for a conditioning interval that may or may not be followed by a rest interval during which the conditioning current is actively held at zero (0) mA to assist in stabilizing the baseline offset voltage. The length of the conditioning interval is preferably between about 1 second to about 2 minutes. More preferably, the conditioning interval lasts about 5 seconds to about 1 minute. Even more preferably, the conditioning interval lasts about 10 seconds to about 30 seconds. The length of the rest interval can be varied from about 0+ seconds up to about 2 minutes. More preferably, the rest interval lasts about 5 seconds to about 15 seconds.

Figure 4:
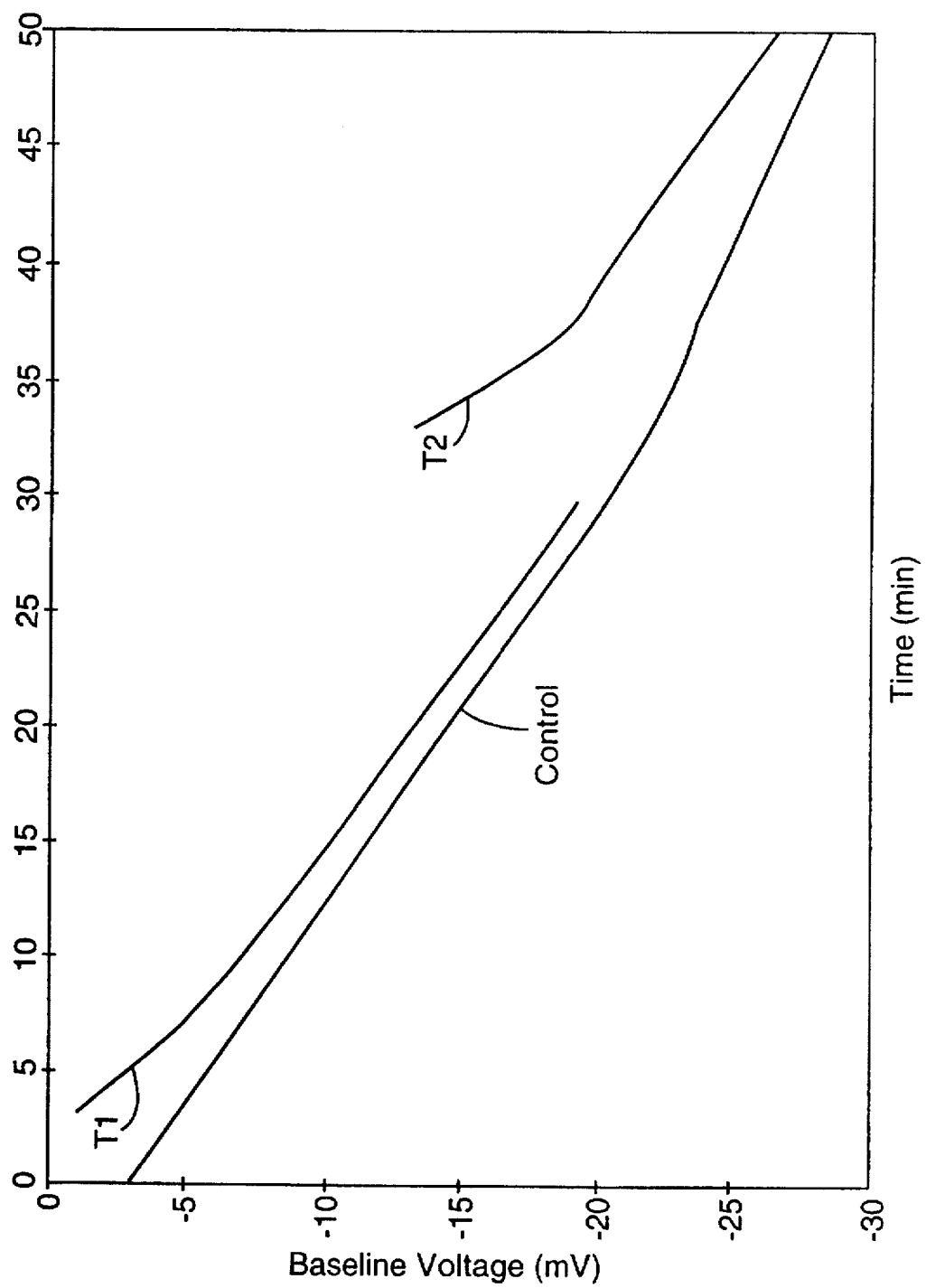
FIG. 4 is a graph of baseline voltage across human skin as a function of time after application monitoring electrode.

By reducing skin impedance, the systems and methods according to the present invention provide an additional advantage in that the baseline offset voltage drift typically experienced when using medical electrodes can also be reduced. FIG. 4 is a graph representing baseline offset voltage across human skin as a function of time after application of a monitoring electrode. Baseline offset voltage is defined as the voltage difference between a test electrode and another similar electrode applied on the body at a skin site abraded with an abrader pad to reduce the resistance of the stratum corneum. The preferred abrader pad used in conjunction with the reference electrodes is a ONE STEP™ abrading material marketed by Minnesota Mining and Manufacturing Company, St. Paul, Minn.

As depicted, the magnitude of baseline offset voltage naturally increases from near 0 mV to near −30 mV over a period of about 50 minutes. In large part, the drift in baseline offset voltage is due to increases in the magnitude of $i_{electrolyte}$ as discussed above with respect to Equation 2. The increase in magnitude of the baseline offset voltage increases the magnitude of skin deformation artifact.

When a conditioning current is applied through the electrodes, the baseline offset voltage between a test electrode placed on untreated skin, i.e., skin that has not been abraded, can be substantially reduced towards zero or even slightly positive. By proper application of conditioning currents, whether intermittently, periodically or continually, it should be possible to maintain the baseline offset voltage in the range of about +10 mV, more preferably in the range of about +5 mV.

In FIG. 4, line T1 depicts the results on baseline voltage of an initial conditioning current application of about 0.33 mA/cm$^2$ of direct current for 1 minute followed by a 0 mA rest interval for 30 seconds. The initial conditioning current reduced the baseline voltage to about less than −5 mV, after which it drifted to about −18 mV after about 30 minutes. A second conditioning current was provided according to the protocol used to provide the first conditioning current at 30 minutes after placement of the electrode. Referring to line T2 in FIG. 4, application of that second conditioning current reduced the baseline offset voltage to about −12 mV immediately after the zero (0) mA rest interval current was applied.

Because the baseline voltage drift is typically towards the negative, it is preferred that the conditioning currents have anodic polarity to offset, or correct for, the negative drift. Application of a conditioning current with cathodic polarity may actually increase the negative drift of the baseline voltage.

In addition to the conditioning current delivered during the conditioning interval and rest interval (if any), additional electrical energy in the form of a background current can also be provided by the systems and methods according to the present invention. The background current is preferably an anodic direct current with a constant amplitude of about 0 nA/cm$^2$ to about 10 µA/cm$^2$. By constantly applying a small anodic background current, the baseline offset voltage drift can be reduced due to the positive (anodic) charges applied through the background offset the natural negative drift of the baseline offset voltage. By reducing the baseline offset voltage, the background current further reduces deformation artifact as discussed in connection with Example 2 below. Although an anodic direct current is preferred, it will be understood that any suitable waveform may be used to provide the desired background current, provided that the baseline offset voltage is reduced by the background current.

An advantage of the present invention is a significant reduction in skin impedance and corresponding deformation artifact without any site preparation such as abrasion, piercing or the application additional electrolyte materials.

Because the skin need not be physically prepared through abrasion or piercing, another advantage of the present invention is that the irritation and discomfort associated with abrasion and/or piercing of the patient's skin are avoided.

Yet another advantage is that the present invention need not rely on the skin preparation skills of the operator attaching the electrodes to effectively reduce skin impedance and deformation artifact. In those approaches to reducing skin impedance, the skill level of the operator significantly effects the reliability of the procedure as well as the patient's comfort.

Still another advantage is that the present invention can be used to quickly and automatically reduce skin impedance, thereby preventing saturation of the amplifier in the monitor and providing accurate trace signals shortly after application of the electrodes to a patient. This ability is critically important in emergency situations such as cardiac defibrillation.

As an example of this problem, one popular monitor (manufactured by Hewlett-Packard Co. under the tradename MERLIN) provides a small cathodic direct current for monitoring at about −67 nA to measure resistance at the electrode-skin interface to provide the user with an indication as to whether an electrode has fallen off of a patient, whether a lead has fallen off of an electrode, whether a lead wire is broken, or if the electrode-skin resistance is so high as to prevent accurate monitoring of bioelectric signals.

The amplifiers used in that monitor, however, can tolerate an input signal voltage of a relatively small amplitude, i.e., about 540 mV. In many situations, the electrode-skin impedance level is high enough immediately upon application of the electrodes to cause the voltages developed by the −67 nA monitoring current to exceed input signal voltage levels of the monitor. This causes a saturation of the amplifier, leading to the display of a flat line instead of a regular electrocardiogram rhythm This condition can be serious in an emergency as it mimics the condition of a heart that is not beating and may cause the patient to receive inappropriate therapy.

Other situations in which the reduction of skin deformation artifact is especially helpful is in the monitoring of bioelectric signals during emergency transport situations during which a patient is not at rest, during stress testing when the patient is in constant motion, or during Holter/ambulatory monitoring of bioelectric signals such as electrocardiograms to assist in the diagnosis of cardiac irregularities.

In addition, even when no obvious artifact such as those described herein are present, high skin impedance can distort the low frequency components of the electrocardiogram, such as the S-T segment. These distortions can result in a misdiagnosis, but are reduced by lowering the skin impedance according to the present invention.

A further feature of the present invention is that by applying a conditioning current with the proper polarity, the systems and methods according to the present invention can provide for reconditioning of electrodes having a silver-silver chloride composition. The advantage of silver-silver chloride electrodes is that they are non-polarizing due to the presence of AgCl. If, however, sufficient cathodic current is passed through an electrode, either during a defibrillation procedure or during other events the proportion of AgCl can be depleted. An anodic conditioning current or charge can, however, cause a proportional formation of AgCl on the electrode. As a result, two functions can be achieved using an anodic conditioning current—skin impedance can be reduced and the non-polarizing characteristics of Ag—AgCl electrodes can be maintained. It will, however, be understood that care should be exercised not to form too much AgCl as that may negatively affect the electrical properties of the electrode.

It will also be understood that this method of reconditioning electrodes can be used with any non-polarizable electrode other than Ag—AgCl, one example of which is a redox couple electrode as described in U.S. Pat. No. 4,846,185.

An additional advantage is that the baseline can be reestablished sooner after the passage of a polarizing current such as a defibrillation pulse by passing a current with the proper polarity through the electrode immediately after the polarizing event.

As discussed above, the systems and methods according to the present invention reduce skin impedance by driving a small amount of electrical energy, referred to as a conditioning current, through a medical electrode and into the patient's skin. The conditioning current can be provided in any waveform, direct or alternating current, and the waveforms can be provided intermittently, periodically at predetermined intervals, or continually if desired. In some instances, the waveform may even be generated by noise, i.e., there is no requirement that the waveform be regular in any way provided the necessary amount of electrical energy is passed through the electrode-skin interface.

Figure 5:
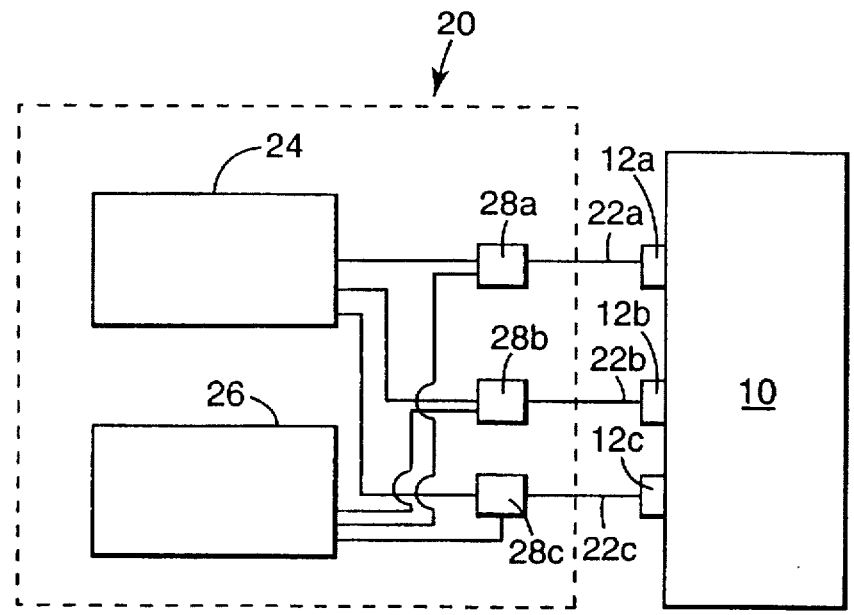
FIG. 5 is a schematic representation of one system according to the present invention.

FIG. 5 is a schematic diagram of one system according to the present invention. The system 20 includes bioelectric signal monitoring circuitry 24, as well as conditioning current supply 26 for providing the desired conditioning current and, if applicable, the background current. Both the monitoring circuitry 24 and the conditioning current supply 26 are attached to medical electrodes 12a, 12b and 12c (collectively referred to as electrodes 12) that are located on a patient's skin 10. One of the electrodes 12 will typically be designated as the return electrode while the other electrodes 12 are provided to monitor the bioelectric signals. Although only two monitoring electrodes are depicted, it will be understood that any number of electrodes 12 could be provided for use in systems and methods according to the present invention.

The electrodes 12 are attached to system 20 by leads 22a, 22b and 22c (collectively referred to as leads 22). In the depicted system 20 according to the present invention, relays 28a, 28b and 28c (collectively referred to as leads 28) are provided between the leads 22 to allow for switching between the conditioning current supply 26 and the monitoring circuitry 24. This arrangement protects the monitoring circuitry 24 from the electrical energy provided by conditioning current supply 26 which could, in some instances, damage the monitoring circuitry 24.

The relays 28 may also be useful for providing conditioning currents to each of the electrodes 12 in sequence (i.e., consecutively), in groups, or to all electrodes 12 simultaneously. Any desired protocol can be administered according to the needs and desires of the user.

Although the conditioning current supply 26 is depicted as included in an integrated system 20 along with the monitoring circuitry 24, it should be understood that the conditioning current supply 26 could be provided separately from the monitoring circuitry 24. If provided separately, the conditioning current supply 26 could be located along the leads 22 connecting the electrodes 12 to the monitoring circuitry 24. As a result, the conditioning current supply 26 could be used to retrofit existing monitors.

Although leads are depicted in FIG. 5, it will be understood that the systems and methods according to the present invention are equally applicable to wireless systems in which the bioelectric signals are transmitted to remote monitors using telemetry equipment. In such a system, the conditioning current source would need to be mounted on or near the electrodes.

The system 20 may also include circuitry designed to monitor skin impedance levels continuously, periodically, intermittently or on demand by the user. Alternatively, the system 20 could include adaptive intelligence to provide monitoring of skin impedance and/or baseline offset voltage and vary the application of any conditioning and/or background current to control those factors.

Another variable that could be monitored by the system is the algebraic sum of the charges passed through each electrode to maintain the non-polarizing properties of an electrode. That value could then be used as a basis for providing currents of the proper polarity, as necessary, to recondition the electrode, e.g., as discussed above with respect to Ag—AgCl electrodes.

At one level, it may be advantageous to simply control skin impedance to prevent saturation of, for example, monitoring equipment. Equation 4 below depicts the preferred relationship between the variables needed to prevent saturation of monitoring equipment:

$$Z < V_{saturation} / \Sigma(i_{DC} + i_{AC}) \qquad \text{(Equation 4)}$$

where $V_{Saturation}$ is the saturation voltage of the monitoring circuitry, $i_{DC}$ are the direct currents passing through the electrodes and $i_{AC}$ are the alternating currents passing through the electrodes.

Because the effect of some alternating currents such as a high frequency respiratory monitoring circuit is relatively small as compared to direct currents for determining skin impedance levels, Equation 4 can generally be represented more simply by Equation 5 below:

$$R < V_{saturation} / \Sigma i_{DC} \qquad \text{(Equation 5)}$$

It will be understood that some alternating currents with lower frequencies may also contribute to saturation of the monitoring circuits and may also need to be considered in Equation 5.

As a result, the monitoring of skin impedance can effectively be accomplished by measuring skin resistance R beneath the medical electrodes to determine whether application of a conditioning current is needed to provide the advantages of the present invention.

Methods and circuitry for measuring the resistance between an electrode and skin are well known to those skilled in the art and will not be described in detail herein.

Medical electrodes 12 can take many different forms, including disposable electrodes, reusable electrodes, and variations of both disposable or reusable electrodes. In addition, the electrodes could also be similar to those that combine more than one function, such as monitoring, defibrillation, and/or pacing. One example of a multi-functional electrode is described in WO 94/26950, a PCT patent application published on 24 Nov. 1994. Furthermore, the electrodes may include conductive gels, conductive adhesives or any other substances required for monitoring bioelectric signals through the skin.

Furthermore, the present invention is useful to reduce skin impedance for the monitoring any bioelectric signal activity, including electrocardiograms (ECG), electromyograms (EMG), electroencephalograms (EEG), and other sources of bioelectric signals which are desirably measured through the use of electrodes placed on a patient's skin.

Although not shown in FIG. 5, the present invention is also useful in systems including a driven-right-leg circuit to reduce artifacts due to alternating current power sources, static voltages, and radio frequency sources. In addition, shielding can also be used to protect against additional noise, as well as taking actions to reduce the components of noise due to magnetic fields, and triboelectric voltages being induced in the circuit. As described above, however, none of these methods reduces the major source of artifact in the signal, i.e., the artifact associated with skin deformation. In combination with the present invention, however, these additional measures can provide a trace for monitoring bioelectric signals with excellent trace quality.

In some instances, a subject may experience discomfort on application of the conditioning current. Ramping up of the conditioning current may prevent unnecessary discomfort, but another approach at reducing any discomfort associated with application of a conditioning current according to the present invention may include an electrolyte composition used in conjunction with medical electrodes that includes one or more agents to reduce discomfort in a patient. A further advantage of incorporating agents into the electrolyte solution is to allow for faster increases in the amplitude of the conditioning current, thereby, also providing a faster reduction in skin impedance.

Agents that may be useful to reduce discomfort can include those known to possess the following properties when applied to skin: anti-inflammatory, antihistamine, analgesic or anesthetic. Some substances that possess these properties include diphenyhydramine hydrochloride, zinc acetate, hydrocortisone acetate, benzocaine, lidocaine, or novocaine. An advantage of these agents is that they are all approved for topical application to human skin.

If the electrolyte includes agents to reduce discomfort, the need for ramping up of conditioning currents may be reduced, thereby allowing for quicker reduction of skin impedance by conditioning currents according to the present invention.

It should also be understood that including a discomfort-reducing agent in the electrolyte would also be helpful for electrodes used without a conditioning current to reduce artifact. In those applications, the discomfort associated with placing an electrolyte containing salts on an abraded site can be reduced or eliminated. One particular application where the agent may be especially useful in an electrolyte is when the electrode is used to provide an electroencephalograph (EEG). Because the biopotentials monitored in EEG's are in the microvolt range, the skin impedance is typically reduced using a blunt hypodermic needle that is twirled on the skin, often breaking the skin. By incorporating an agent into the electrolyte, the discomfort associated with this procedure can be reduced.

Many of the agents listed above are available over-the-counter in preparations for topical application to provide relief from insect bites, allergic skin responses and other conditions. One such topical preparation is marketed under the tradename Sting-Eze by Wisconsin Pharmaceutical Co. Inc. of Jackson, Wis. Its ingredients include liquefied phenol, benzocaine, diphenyhydramine hydrochloride, and minor amounts of eucalyptus and propylene glycol. Another preparation is marketed under the tradename Benadryl by Parke-Davis Inc., of Morris Plains, N.J. This preparation includes diphenyhydramine HCl as its primary active ingredient.

The following non-limiting example is provided to illustrate one application of an electrolyte containing an agent to reduce discomfort.

EXAMPLE 1

A 0.3 g amount of the Sting-Eze preparation was added to a 1 g sample of guar gum gel (without borate) of a Red Dot Electrode (No. 2259, manufacturing by Minnesota Mining and Manufacturing Company, St. Paul, Minn.) and mixed well. This gel is described in U.S. Pat. No. 4,406,827. The gel included ~2% guar gum, 3% KCl, 12% propylene glycol, 0.02% $NaClO_2$, and the balance water.

A site on the left inner forearm of a human subject was abraded with the abrader pad from the electrode. Up to 15–20 strokes were used to abrade the site with a ONE STEP™ abrader pad. A sample of the gel without the Sting-Eze preparation was applied to the abraded site. Within a few seconds the subject experienced a burning/itching sensation.

The gel was then wiped off the site cleansed with distilled water and wiped dry. The sample of guar gum gel containing the Sting-Eze was then applied to the same abraded site. The subject experienced no itching or burning sensation even after several minutes.

The following non-limiting examples are provided to illustrate the effect of some conditioning currents on skin deformation voltage artifact.

EXAMPLE 2

Red Dot solid gel electrodes (No. 2259, manufacturing by Minnesota Mining and Manufacturing Company, St. Paul, Minn.) were used as follows:

A reference electrode 32a was attached at an abraded skin site, an auxiliary electrode 32b was attached at an abraded skin site, and a test electrode 32c was applied to unprepared skin. The electrodes will be collectively referred to as 32 below. The abraded skin sites were prepared using a ONE STEP™ abrader pad with a minimum of three strokes. All of the sites were located on the inner forearm of a human subject.

Figure 6:
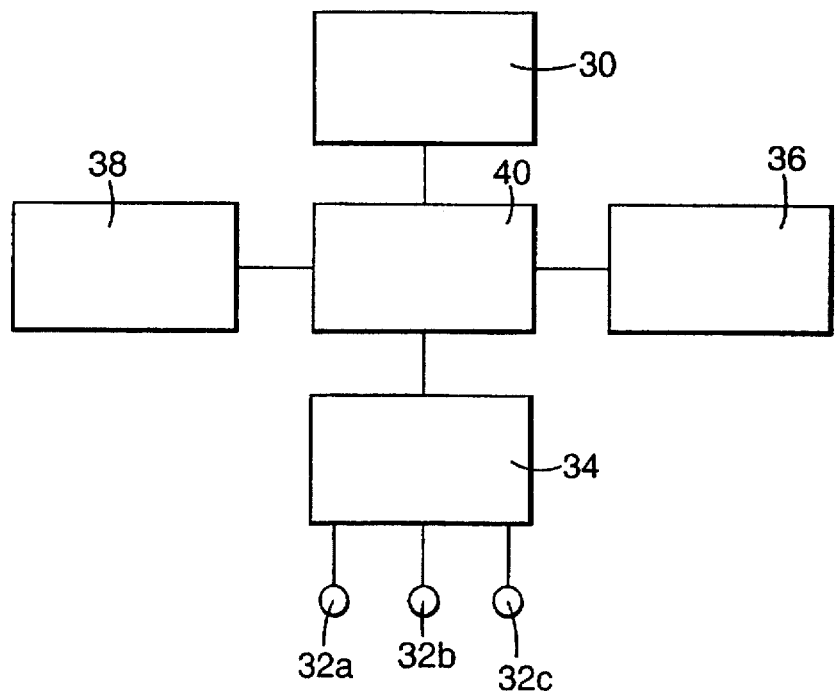
FIG. 6 is a schematic diagram of the apparatus used in Example 2.

FIG. 6 is a schematic diagram of the monitoring apparatus used to take the measurements described herein. The data was acquired with a computer 30 running LAB-VIEW software marketed by National Instruments, Austin, Tex.

The electrodes 32 were connect to a Hewlett-Packard Switch Control 34 (Model HP 3488A), that controlled connections amongst the conditioning current source 36, the impedance analyzer 38, and the interface unit 40 upon command from the computer 40.

The current source 36 was Keithley Model 220 Current Source, marketed by Keithley in Aurora, Ill. The impedance analyzer 38 (Hewlett-Packard Co. Model 4192 A) was also connected to the electrodes 32 through the interface unit 40. The interface unit 40 provided a buffer amplifier to the electrodes 32 and a weight on/off signal to the computer 30.

The following default parameters were set up in the software: conditioning current amplitude for conditioning interval=1 mA; conditioning current amplitude for rest interval=0 mA; maximum compliance voltage=40 V; time duration of conditioning current during conditioning interval=60 seconds; time duration of conditioning current during rest interval=30 seconds.

After setting up the software and attaching the test electrode, a period of about 4 minutes was allowed to pass after which the impedance analyzer was used to measure the resistance between the test electrode and reference electrode.

The program was then started and baseline offset voltage was measured beneath the test electrode. After five seconds, a 500 gram weight was placed on the test electrode for 15 seconds after which it was removed. The electrical contact between the metal of the weight and the lead attached to the electrode was used in a circuit (not shown) to signal placement and removal of the weight on the test electrode.

Figure 7:
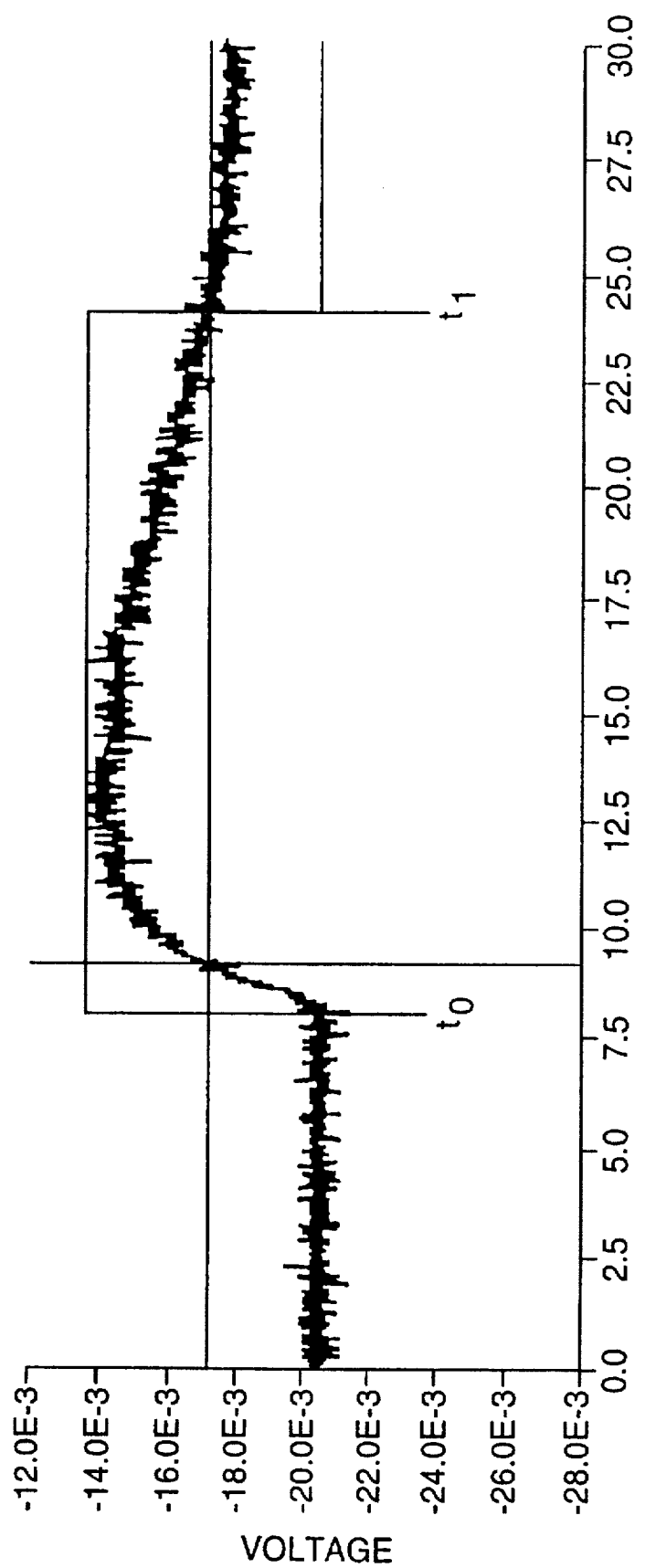
FIG. 7 is a real-time graph of skin deformation voltage artifact versus time depicting the variation in deformation voltage over time for a single deformation.

The computer then processes the data and displays a real-time graph of skin deformation voltage artifact versus time depicting the variation in deformation voltage over time for a single deformation. One example of such a graph is shown in FIG. 7.

Figure 8:
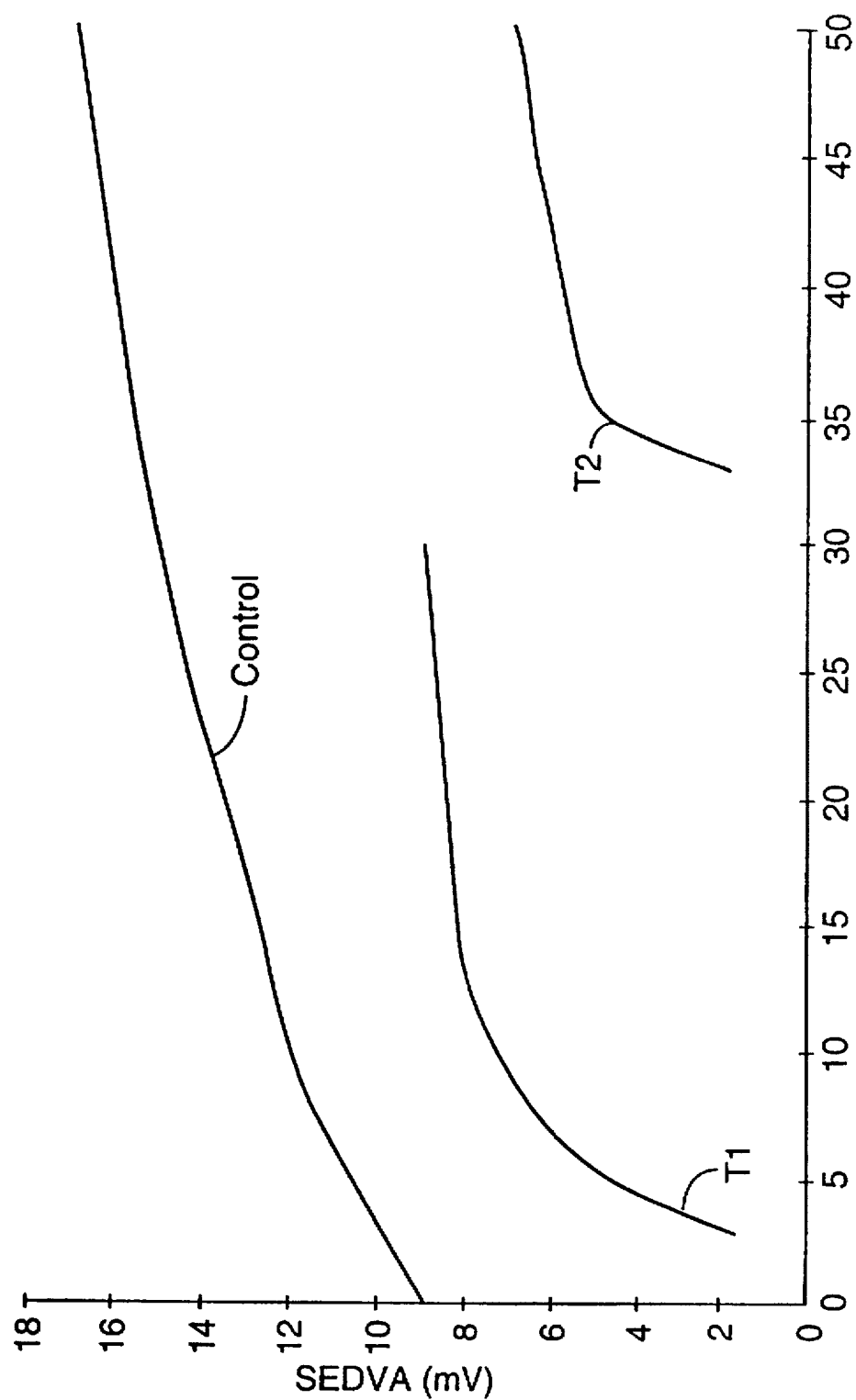
FIG. 8 is a graph depicting measurements of skin deformation voltage artifact taken according to Example 2 both with and without application of conditioning currents.
Figure 9:
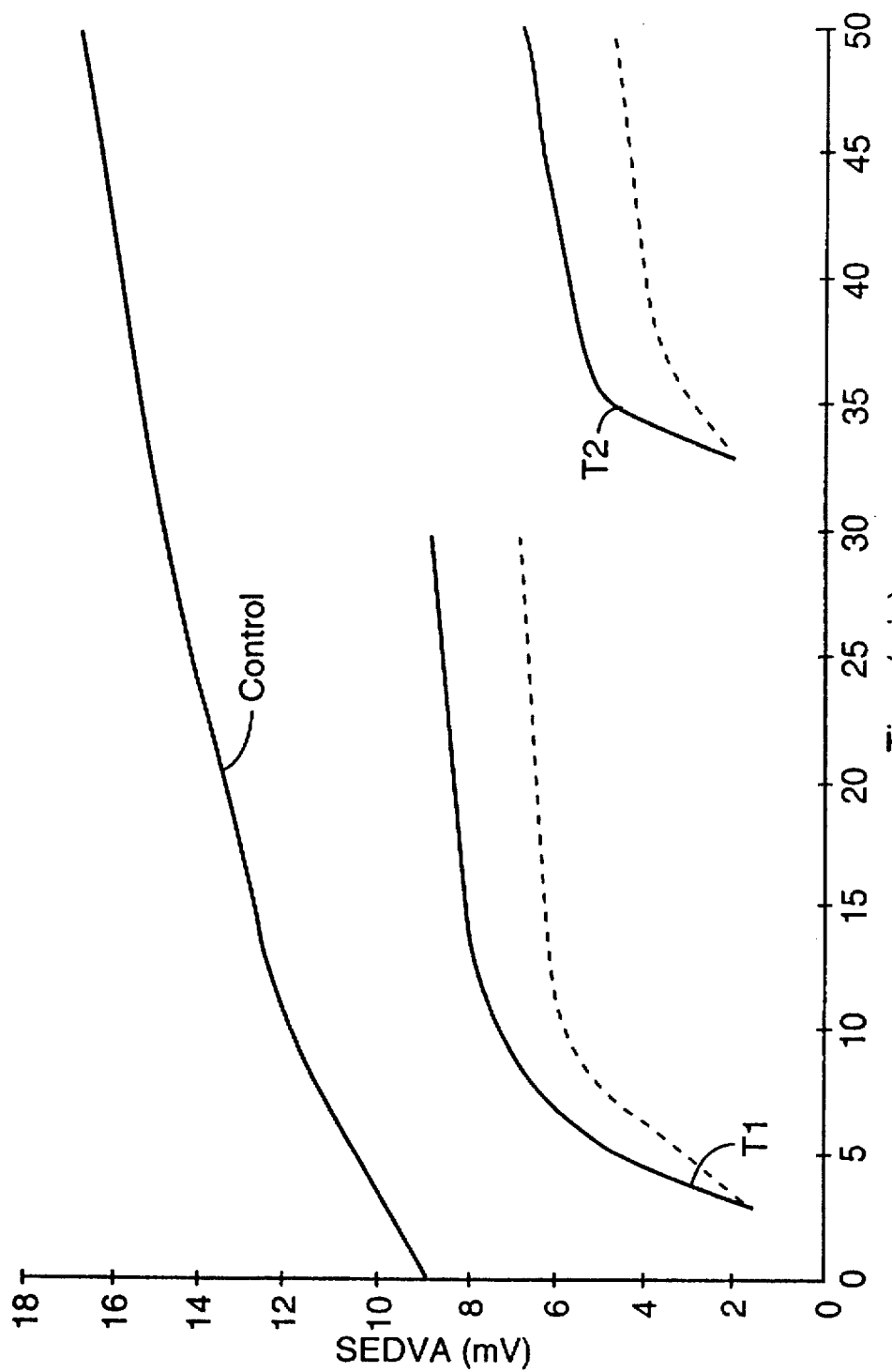
FIG. 9 is a graph depicting measurements of skin deformation voltage artifact taken according to Example 3 both with and without application of conditioning currents.

By repeatedly deforming the skin using the weight and measuring deformation voltage artifact due to that deformation, the control line depicted in FIG. 8 can be obtained (i.e., it is a composite of numerous data points). As shown, the deformation voltage artifact increases over time (in spite of the decrease in skin resistance as depicted in FIG. 3).

13

Line T1 in FIG. 8 shows the effect of an initial application of a conditioning current through the test electrode on deformation voltage artifact as measured periodically to provide the line T1. The conditioning current consisting of a 1 mA anodic direct current was passed through the test electrode via the auxiliary electrode for 60 seconds (the conditioning interval), followed by application of the 0 mA current for the 30 second rest interval.

As shown by line T1, deformation voltage artifact increase over time, but still remains lower than the control value. Also shown in FIG. 8 is a second application of a conditioning current to reduce the deformation voltage artifact which causes a second drop in skin deformation voltage artifact represented by line T2.

Taken together, lines T1 and T2 show the benefit of intermittently applying a conditioning current to lower skin deformation voltage artifact.

The work was repeated using electrodes having conductive adhesive and similar results were achieved.

EXAMPLE 3

The equipment and methods used in Example 2 were again used in this example. The difference is that a background current of 1 μA (anodic direct current) was applied through the test electrode immediately after the cessation of the rest interval and until the beginning of the next application of the conditioning current. The effect of that application on skin deformation voltage artifact is shown in the dashed lines below T1 and T2, where it can be seen that skin deformation voltage artifact is further reduced.

The present invention has been described above with respect to illustrative systems and methods to which modifications may be made without departing from the scope of the invention as defined by the appended claims.

What is claimed is:

1. A method of conditioning skin to reduce artifact in bioelectric signal monitoring through an electrode on skin comprising the steps of:

14 a) placing the electrode on the skin; and
b) conditioning the skin beneath the electrode by passing electrical energy at a rate of about 5 μA/cm$^2$ to about 5 mA/cm$^2$ through the electrode and into the skin using a ramped conditioning current to reduce skin impedance.

2. The method according to claim 1, further comprising a step of monitoring a bioelectric signal through the electrode.

3. The method according to claim 2, wherein the electrical energy is passed for about 1 second to about 2 minutes.

4. The method according to claim 1, wherein the step of passing electrical energy comprises passing electrical energy at a rate of about 100 μA/cm$^2$ to about 1.5 mA/cm$^2$.

5. The method according to claim 1, wherein the ramped conditioning current also includes a ramping down of amplitude towards zero.

6. The method according to claim 1, wherein the step of conditioning further comprises passing a electric energy at a first rate through the electrode for a first predetermined time interval followed by a second predetermined rest interval during which the amplitude of electric current passing through the electrode is held at about zero.

7. The method according to claim 6, further comprising the step of passing a background current through the electrode and into the skin, the background current comprising an anodic direct current.

8. The method according to claim 7, wherein the background current has a maximum amplitude of up to about 10 μA/cm$^2$.

9. The method according to claim 1, wherein the electrical energy is supplied by a current having a waveform chosen from the group consisting of direct current, square waves, rectangular waves, saw-toothed waves, sinusoidal waves which do not reverse polarity, rectified sinusoidal waves, and arbitrary/random waveforms.

10. The method according to claim 1, wherein the electrical energy is chosen from the group consisting of anodic direct current and cathodic direct current.

\* \* \* \* \*